United States Patent [19]
Costa et al.

[11] Patent Number: 5,545,529
[45] Date of Patent: Aug. 13, 1996

[54] ASSAY FOR DETECTING COVALENT DNA-PROTEIN COMPLEXES

[75] Inventors: Max Costa, Ramsey, N.J.; Anatoly V. Zhitkovich, Greenwood, N.Y.

[73] Assignee: New York University, New York, N.Y.

[21] Appl. No.: 410,389

[22] Filed: Mar. 27, 1995

Related U.S. Application Data

[63] Continuation of Ser. No. 8,794, Jan. 27, 1993, abandoned.
[51] Int. Cl.$^6$ .............................. C12Q 1/48; C12Q 1/68; C12Q 1/533
[52] U.S. Cl. .................................. 435/6; 435/15; 530/358
[58] Field of Search .......................... 435/6, 15; 530/358; 514/44

[56] References Cited

FOREIGN PATENT DOCUMENTS

WO90/04650  5/1990  WIPO.

OTHER PUBLICATIONS

Zhitkovics et al. Carcinogeney 13: 1485–1489 (1992).
Costa, M., "Analysis of DNA–Protein Complexes Induced by Chemical Carcinogens", *Journal of Cellular Biochemistry (1990) 44:127–135*.
Liu et al., "Cleavage of DNA by Mammalian DNA Topoisomerase II", *Journal of Biological Chemistry* (1983) 258:15365–15370.
Muller, M. T., "Nucleosomes Contain DNA Binding Proteins that Resist Dissociation by Sodium Dodecyl Sulfate", *Biochemical and Biophysical Research Communications* (1983) 114:99–106.
Trask et al., "Rapid detection and isolation of covalent DNA/protein complexes: application to topoisomerase I and II", *EMBO Journal* (1984) 3:671–676.
Rowe et al., "DNA Damage by Antitumor Acridines Mediated by Mammalian DNA Topoisomerase II", *Cancer Research* (1986) 46:2021–2026.

Sugiyama et al., "Characterization of DNA Lesions Induced by $CaCrO_4$ in Synchronous and Asynchronous Cultured Mammalian Cells" *Molecular Pharmacology (1986) 29:606–613*.
Banjar et al. "cis–and trans–Diamminedichloroplatinum(II)–Mediated Cross–Linking of Chromosomal Non–Histone Proteins to DNA in HeLa Cells" *Biochemistry* (1984) 23:1921–1926.
Banjar et al., "Crosslinking of Chromosomal Proteins to DNA in HeLa Cells by UV, Gamma Radiation and Some Antitumor Drugs" *Biochemical and Biophysical Research Communications* (1983) 114:767–773.
Patierno et al., "Effects of Nickel(II) on Nuclear Protein Binding to DNA in Intact Mammalian Cells" *Cancer Biochem Biophys.* (1987) 9:113–126.
Patierno et al., "DNA–Protein Cross–Links Induced by Nickel Compounds in Intact Cultured Mammalian Cells" *Chem.–Biol. Interactions (1985) 55:75–91*.
Kohn et al., "Measurement of Strand Breaks and Cross–Links by Alkaline Elution" *DNA Repair: A Laboratory Manual of Research Procedures* (1981) 1:379–401 Part B.

(List continued on next page.)

*Primary Examiner*—W. Gary Jones
*Assistant Examiner*—Paul B. Tran
*Attorney, Agent, or Firm*—Morrison & Foerster LLP

[57] ABSTRACT

Since sodium dodecyl sulfate (SDS) binds tightly to proteins but not to DNA, the addition of potassium chloride (KCl) to SDS lysates of cells, nuclei or mitochondria results in the formation of an insoluble precipitate which includes all proteins and detergent-resistant DNA-protein complexes separated from free DNA in the supernatant. The amount of SDS-precipitable DNA represents a measure of crosslinked DNA-protein. This precipitation method is useful for determining or quantitating crosslinked DNA-protein formed in cells, nuclei or mitochondria of animals following their exposure to crosslinking agents such as chromate, nickel, cis-Pt (II) diammine dichloride and formaldehyde. The method is also useful for evaluating agents for their ability to induce covalent DNA-protein crosslinking.

26 Claims, 6 Drawing Sheets

OTHER PUBLICATIONS

Kohn et al., "DNA–Protein Crosslinking By *trans*-Platinum(II Diamminedichloride in Mammalian Cells, A New Method of Analysis" *Biochimica et Biophysica Acta* (1979) 562:32–40.

Chiu et al., "Differential processing of ultraviolet or ionizing radiation–induced DNA–protein cross–links in Chinese hamster cells" *Int. J. Radiat. Biol.* (1984) 46:681–690.

Cohen et al., "A Blotting Method for Monitoring the Formation of Chemically Induced DNA–Protein Complexes" *Analytical Biochemistry* (1990) 186:1–7.

Miller et al., "Analysis of Proteins Cross–Linked to DNA After Treatment of Cells With Formaldehyde, Chromate, and *cis*–Diamminedichloroplatinum(II)" *Molecular Toxicology* (1989) 2:11–26.

Miller et al., "Immunological detection of DNA–protein complexes induced by chromate" *Carcinogenesis* (1989) 10:667–672.

Miller et al., "Characterization of DNA–Protein Complexes Induced in Intact Cells by the Carcinogen Chromate" *Molecular Carcinogenesis (1988) 1:125–133.*

Chen et al., " Alteration in restriction enzyme digestion patterns detects DNA–protein complexes induced by chromate" *Carcinogenesis* (1991) 12:1575–1580.

Oleinick et al., "The formation, identification, and significance of DNA–protein cross– links in mammalian cells" Br. J. *Cancer* (1987) 55:135–140.

Wedrychowski et al., "Chromium–induced Cross–linking of Nuclear Proteins and DNA" *Journal of Biological Chemistry* (1985) 260:7150–7155.

Grunicke et al., "Effect of Alkylating Antitumor Agents on the Binding of DNA to Protein" *Cancer Research* (1973) 33:1048–1053.

Cosma et al., "Growth inhibition and DNA damage induced by benzo[a]pyrene and formaldehyde in primary cultures of rat tracheal epithelial cells" *Mutation Research* (1988) 201:161–168.

ASSAY FOR DETECTING COVALENT DNA-PROTEIN COMPLEXES

This invention was funded in part by research grants from the U.S. National Institute of Environmental Health Sciences and the U.S. Environmental Protection Agency, which provides to the United States Government certain rights in the invention.

This application is continuation of application Ser. No. 08/008,794, filed Jan. 27, 1993 now abandoned.

TABLE OF CONTENTS

1. INTRODUCTION
2. BACKGROUND OF THE INVENTION
   2.1 DNA-PROTEIN CROSSLINKING
   2.2. DETECTION OF DNA-PROTEIN COMPLEXES
3. SUMMARY OF THE INVENTION
4. BRIEF DESCRIPTION OF THE DRAWINGS
5. DETAILED DESCRIPTION OF THE INVENTION
6. EXAMPLE: CROSSLINKING OF DNA-PROTEIN IN CULTURED CELLS
   6.1. DETECTION OF DNA-PROTEIN CROSSLINKS
   6.2. CELL GROWTH
   6.3. Cis-Pt Treatment
   6.4. Formaldehyde Treatment
   6.5. Chromate Treatment
7. EXAMPLE: TREATMENT OF ANIMALS WITH CROSSLINK-INDUCING AGENTS
8. EXAMPLE: DETECTION OF DNA-PROTEIN CROSSLINKS IN METAL WELDERS
   8.1. Methods
   8.2. Results and Discussion

1. INTRODUCTION

The invention in the field of biochemistry relates to a novel method, noted for its simplicity and economy, for detecting covalent DNA-protein binding including that which has occurs in cells. Such crosslinking is often induced by various forms of irradiation or by chemical carcinogens or other chemical compounds. The method further allows detection of DNA-protein crosslinking caused by exposure of an animal to a crosslink inducing agent. The method is based on precipitation of proteins, including those covalently bound to DNA, by potassium-sodium dodecyl sulfate after harsh treatment of a preparation to dissociate all non-covalently bound protein from DNA.

2. BACKGROUND OF THE INVENTION

2.1. DNA-PROTEIN CROSSLINKING

DNA-protein interactions are important in almost every aspect of gene expression and inheritance (Stein, G. S. et al., eds., *CHROMOSOMAL PROTEINS AND THEIR ROLE IN THE REGULATION OF GENE EXPRESSION*, Academic Press, New York, 1979) and disruption of normal interactions has serious consequences (Costa, M., *J. Cellular. Biochem.* 44:127–135 (1990)). DNA-protein crosslinks have been shown to be induced by many established or suspected carcinogens such as UV and gamma radiation, BCNU (Banjar, Z. M. et al., *Biochem. Biophys. Res. Commun.* 114:767–773 (1983)), alkylating agents (Grunicke, H. et al., *Cancer Res.* 33:1048–1053 (1973)), formaldehyde (Cosma, G. N. et al., *Mutat. Res.* 201:161–168 (1988)) and some metal compounds such as nickel (Patierno, S. R. et al., *Chem. Biol.* Interactions 55:75–91 (1985)), chromate (Wedrychowski, A. et al., *J. Biol. Chem.* 260:7150–7155 (1985)), (Sugiyama, M. et al., *Mol. Pharmacol.* 29:606–613 (1986)) and cis- or trans-Pt(II) diammine dichloride (Banjar, Z. M. et al., *Biochemistry* 23:1921–1926 (1984)).

Nickel induces DNA-protein crosslinks indirectly via oxygen radicals (Salnikov, K. et al., *Carcinogenesis* 13:2341–2346 (1992)). Chromate can act directly by binding of the trivalent Cr to the phosphate backbone of DNA and linked to proteins through amino acid reactive groups such as the imidazole nitrogen of histidine or the hydroxyl group of tyrosine (Patierno, S. R. et al., supra).

The biological significance of DNA-protein crosslinks in vivo are still poorly understood. DNA-protein crosslinks are persistent in treated cells since their presence can be easily detected at long time intervals following removal of the crosslinking agent (Sugiyama, M. et al., supra; Tsapakos, M. J. et al., *Cancer Res.* 43:5662–5667 (1983)). Due to poor repair capacity, DNA-protein complexes may be present at critical phases of cellular function, e.g., during DNA replication, and thereby result in the loss of genetic material. This could, for example, inactivate tumor suppressor genes and lead to tumor formation. Because of the apparent low capacity for repair, the detection of this type of DNA damage should serve as a potentially important biological marker of exposure to various toxic agents.

2.2. DETECTION OF DNA-PROTEIN COMPLEXES

Many attempts have been made to develop methods of sufficient sensitivity and rapidity for detecting DNA-protein crosslinking occurring in cells exposed to crosslinking agents. The most widely used method for detecting and studying DNA-protein complexes is the alkaline elution method (Kohn, K. W. et al., *DNA Repair: A Laboratory Manual of Research Procedures* 1:378–401 Part B (1981)). The filter retention technique (Chiu, S.-M. et al., *Int. J. Radiat Biol.* 46:681–690 (1984)), as well as several other recently developed methods, have been utilized to detect the formation of DNA-protein complexes in intact cells (Cohen, M. D. et al., *Anal. Biochem.* 186:1–7 (1990); Miller, C. A. et al., *Carcinogenesis* 10:667–672 (1989); Chen, Y. et al., *Carcinogenesis* 12:1575–1580 (1991)). The alkaline elution method, though very sensitive, detects the lesions only indirectly, measuring the velocity at which DNA fragments pass through a filter. Protein-linked DNA passes more slowly than does free DNA (Kohn, K. W. et al., *Biochem. Biophys. Acta* 562:32–40 (1979)). Alkaline elution has a number of disadvantages. It is both time consuming and relatively cumbersome, allowing analysis of only a limited number of samples per assay. The technique does not allow isolation and characterization of DNA-protein complexes. Additionally, in many studies, the lysis stringency utilized has not been sufficient to dissociate all proteins bound non-covalently to DNA. For example, nickel (Ni) compounds induce formation of DNA-protein complexes in cultured cells and animal tissues as assessed by alkaline elution assay (Patierno, S. R. et al., supra); Cicarelli, R. B. et al., *Cancer Res.* 42:3544–3549 (1982)). However, using the alkaline elution assay, Ni-induced DNA-protein crosslinks detected with the detergent sarcosyl were disrupted by inclusion of the more stringent detergent, sodium dodecyl sulfate (SDS) at a 1% (v/v) concentration (Patierno, S. R. et al., *Cancer Biochem. Biophys.* 9:113–126 (1987)). Thus, under certain conditions, the results obtained using the alkaline elution method may be influenced by changes in chromatin conformation and/or composition. Therefore, the total DNA-protein complexes observed may not represent true covalent DNA-protein complexes.

A filter-binding technique has been used successfully to quantitate and biochemically characterize DNA-protein crosslinks (Oleinick, N. L. et al., *Br. J. Cancer* 55:135–140 (1987)). However, such measurement usually required high doses of crosslinking agents, and the dissociation conditions were similar to the alkaline elution procedure. In this system, the mechanism by which DNA-protein complexes bound to nitrocellulose filters remained obscure since free DNA did not bind while protein binding was only about 50%.

A number of other assays used to detect DNA-protein complexes (Wedrychowski, A. et al., *J. Biol. Chem.* 260:7150–7155 (1985); Patierno, et al., supra; Miller, C. A. et al., *Mol. Carcinogenesis* 1:125–133 (1988)) provided interesting data about the composition of DNA-protein complexes but also suffered from several disadvantages. They generally utilized ultracentrifugation steps requiring large amounts of starting material, were generally insensitive and were time-consuming.

An additional method for separating covalent DNA-protein complexes from non-covalent DNA-protein complexes was disclosed by Fisher et al., (PCT Publication WO90/04650, 3 May 1990). This method involves treating DNA-protein complexes with a reactive derivative of polyethylene glycol (PEG) to form covalent PEG-protein-DNA complexes which are then separated from DNA not bound to PEG by aqueous phase partition between an aqueous PEG phase and an aqueous phosphate phase. This method was said to allow the partitioning of DNA to which is bound a single protein molecule, such as topoisomerase, if the DNA is short enough. This method is said to be an improvement over the SDS-KCl method of Trask et al., (*EMBO J.* 3:671–676 (1984)) because the latter method is only efficient for sites where many topoisomerase molecules are attached to a single strand of DNA.

The K-SDS assay, above, was successfully used to characterize the covalent complexes formed between pure DNA (plasmid or virus) and topoisomerases in vitro. Sensitivity and reproducibility of this method depended upon DNA fragment size since the presence of a linked protein can precipitate different amounts of DNA depending upon its size. In the setting of pure DNA and protein, fragment size and background DNA-protein crosslinking were not a problem. However, use of a K-SDS assay to determine crosslinked DNA-protein in cell Freparations presents an additional set of hurdles which were overcome by the present invention.

Rowe, T. C. et al., *Cancer Res.* 46:2021–2026 (1986), adapted the K-SDS assay to quantitate DNA-topoisomerase complexes formed following exposure of L1210 cells to acridine derivatives. However, initial attempts by the present inventor to use the Rowe et al. modification of the K-SDS procedure to determine DNA-protein crosslinks in HOS and CHO cells were not successful because of the large amounts of precipitable DNA in untreated cells and the low reproducibility of the method. Additionally, the protocol disclosed for L1210 cells included the addition of salmon sperm DNA to ensure effective washing of the SDS pellet. This step precludes the measurement of non-radioactive (unlabeled) DNA for assessing crosslinking.

In general, the paucity of knowledge about the lesions which result from the covalent crosslinking of DNA with protein is due in part to the unavailability of a rapid, sensitive and simple method for detecting covalent DNA-protein complexes which could be used for early detection of damage in individuals exposed to metals through environmental contact. In particular, individuals occupationally exposed to metals, for example welders exposed to fumes containing various metal oxides and salts, would benefit from such a method. The present invention is directed to solving this problem.

3. SUMMARY OF THE INVENTION

Figure 1:
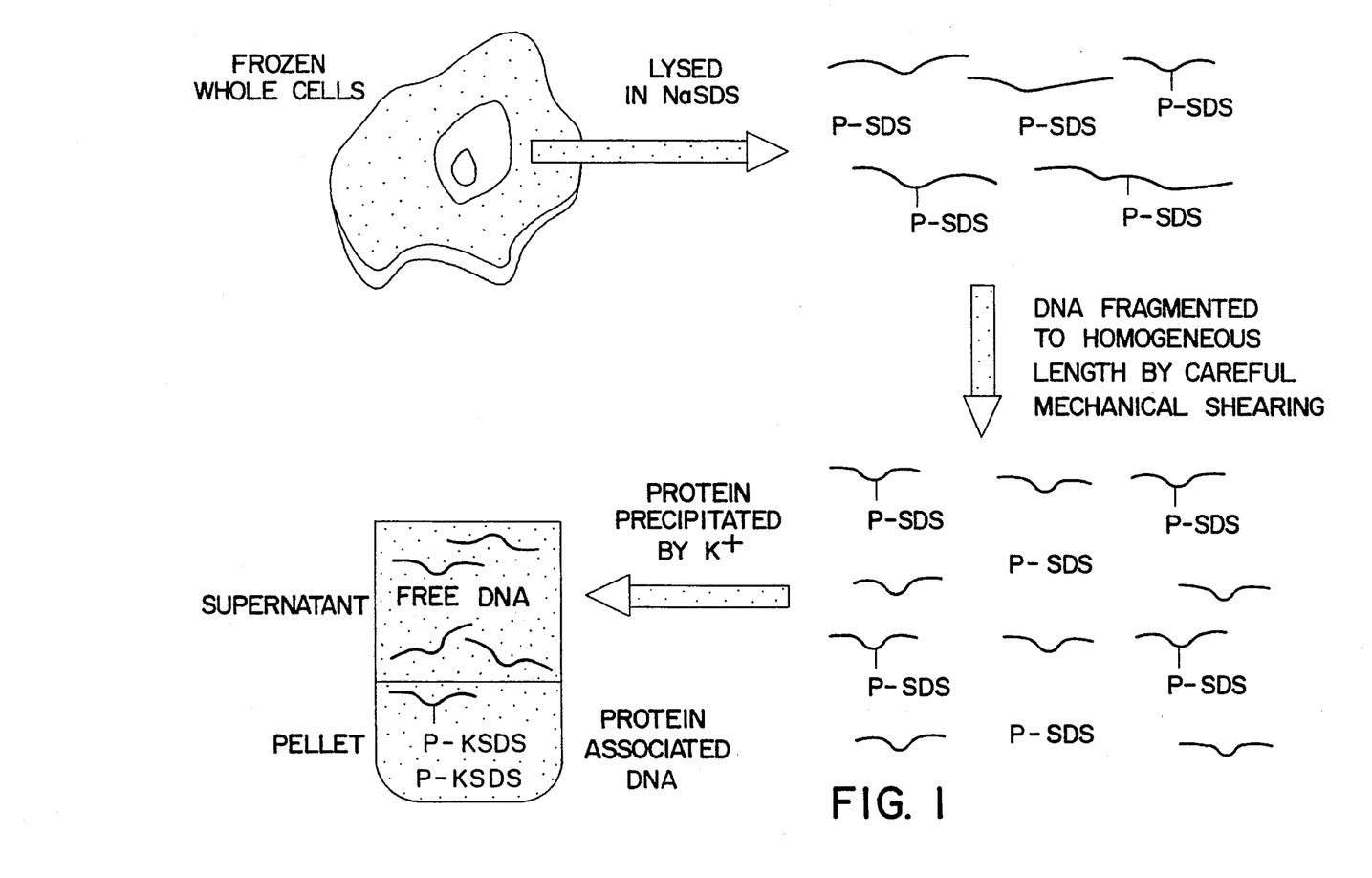

The present inventor has improved the methods described above and has devised a method in which the addition of potassium chloride (KCl) to sodium dodecyl sulfate (SDS)-treated cells results in the formation of an insoluble precipitate of proteins and effectively co-precipitates covalently linked DNA-protein complexes. Measurement of the amount of SDS-precipitable DNA thus represents a measure of DNA-protein crosslinking. This approach is schematically illustrated in FIG. 1. The present inventor has adapted this method to preparing tissue, cells, nuclei or mitochondria for detecting or quantitating covalently bound DNA-protein complexes contained therein and, thereafter determining DNA-protein crosslinks formed in cells following their exposure in culture or in vivo to crosslinking agents such as chromate, cis-Pt (II) diammine dichloride and formaldehyde. Rigorous reproducible shearing of chromosomal DNA and effective washing steps allow the successful application of the K-SDS approach to the assay of DNA-protein crosslinks from cellular preparations. The present method detects in a dose-dependent manner DNA-protein crosslinks induced in cultured CHO cells by chromate, cis-platinum and formaldehyde, This method also successfully detects cross-linked DNA-protein in rat and mouse white blood cells taken from animals exposed in vivo to chromate. The novel method's sensitivity and its simplicity in sample handling and DNA-protein complex isolation potential allows wide application of the assay to measure formation of crosslinked DNA-protein complexes. The ease of recovery of DNA-protein complexes allows for a more thorough investigation of these lesions in cells.

The present invention is thus directed to a method for detecting or quantitating covalently bound DNA-protein complexes, comprising:

(a) treating a sample suspected of containing the DNA-protein complex with SDS at a concentration of at least about 0.5% (v/v) and heat of at least about 65° C. for about 10 minutes under conditions which dissociate proteins from any DNA with which the proteins are non-covalently associated;

(b) co-precipitating all proteins and SDS-resistant DNA-protein complexes in the treated mixture of step (a) by addition of potassium ions to a final concentration of at least about 100 mM;

(c) detecting or quantitating the SDS-precipitable DNA in the precipitate of step (b), wherein the amount of SDS-precipitable DNA is a measure of the covalent DNA-protein complexes.

In a preferred embodiment, the present invention provides a method for detecting in a sample of cells, nuclei or mitochondria covalently bound DNA-protein complexes, comprising:

(a) lysing the cells of the sample in a lysing solution containing at least about 0.5% (v/v) sodium dodecyl sulfate;

(b) adding to the lysate an effective volume of a precipitating solution comprising about 200 mM KCl in about 20 mM Tris-HCl, pH 7.5;

(c) subjecting the mixture to a shearing force produced preferably by freezing at a temperature of −20° C. or less and passing the lysate through a pipet tip at least about five times;

(d) forming a SDS-potassium precipitate by cooling the samples to about 4° C. for about 5 min, and collecting the precipitate;

(e) dispersing the precipitate in a solution of about 100 mM KCl, about 20 mM Tris-HCl, at a pH of about 7.5;

(f) heating the dispersed precipitate to about 65° C. for about 10 minutes followed by cooling to about 4° C. for at least about 5 minutes;

(g) washing the precipitate at least twice more; and (h) resuspending the precipitate in a solution in which the presence or amount of DNA can be determined.

In the above methods, the samples may be frozen and stored, for example at −20° C. or −70° C. after step (a), and the subsequent steps performed after later thawing the samples.

Preferably, in the above embodiment, the lysing solution of step (a) comprises about 2% SDS and about 1 mM phenyl methyl sulfonyl fluoride (PMSF) in a buffer of about 20 mM Tris-HCl, at a pH of about 7.5. The shearing of step (c) is preferably performed under conditions which yield fragments of DNA having an average length of about 20 kilobases.

Also provided herein is a method for detecting covalently bound DNA-protein complexes which have formed in an animal, comprising:

(a) obtaining from an animal suspected of having the DNA-protein complexes a DNA containing sample, preferably cells, cell nuclei or mitochondria (b) detecting or quantitating the complexes in the cells, nuclei or mitochondria according to the above methods.

In a preferred embodiment, the cells obtained from the animal are white blood cells. A preferred animal is a human.

The present invention is also directed to a method for determining whether an animal has been exposed to an agent capable of inducing DNA-protein crosslinking, comprising detecting the presence of, or measuring the quantity of, covalently bound DNA-protein complexes that have been produced in the animal using the method described above. The agent is preferably selected from the group consisting of ultraviolet irradiation, gamma radiation, an alkylating agent, formaldehyde, nickel, chromate, and cis- or trans-Pt(II) diammine dichloride.

Also provided herein is a method for determining the ability of an agent to induce the formation of covalently bound DNA-protein complexes in a sample of cells, nuclei or mitochondria, comprising:

(a) treating the cells, nuclei or mitochondria with the agent under conditions sufficient for the formation of the complexes;

(b) detecting or quantitating the complexes in the treated cells using a method as described above;

(c) detecting or quantitating the complexes in a control sample of cells not treated with the agent using a method as described above; and (d) comparing the results of step (b) and step (c), wherein an increase in the complexes in the treated cells is a measure of the ability of the agent to induce the formation of the DNA-protein complexes.

In the above method, the agent is generally one not known to cause DNA protein complexes but being evaluated for that activity.

In another embodiment, this invention provides a method for determining the ability of an agent to induce the formation of a covalently bound DNA-protein complexes in an animal, comprising:

(a) treating the animal with the agent under conditions sufficient for the formation of the complexes;

(b) detecting or quantitating the complexes formed in the treated animal of step (a) using a method as described above;

(c) detecting or quantitating DNA-protein complexes present in a control animal, not treated with the agent, using a method as described above; and (d) comparing the results of step (b) and step (c), wherein an increase in the complexes from the treated animal is a measure of the ability of the agent to induce the formation of the DNA-protein complexes.

Also provided is a method of isolating DNA complexed with a protein selected from the group consisting of topoisomerase I, topoisomerase II or DNA methyltransferase, comprising:

(a) treating a sample suspected of containing the DNA-protein complex with SDS at a concentration of at least about 0.5% (v/v) and heat of at least about 65° C. for about ten minutes under conditions which dissociate proteins from any DNA with which the proteins are non-covalently associated;

(b) co-precipitating all proteins and SDS-resistant DNA-protein complexes in the treated mixture of step (a) by addition of potassium ions to a final concentration of at least about 100 mM; and (c) obtaining the SDS-precipitable DNA in the precipitate of step (b), and isolating the DNA from the precipitate.

In another embodiment, the present invention is directed to a method of isolating from a sample of cells, nuclei or mitochondria, DNA which was covalently bound to a protein, comprising:

(a) preparing a lysate of the cells, nuclei or mitochondria of the sample in a lysing solution containing at least about 0.5% (v/v) sodium dodecyl sulfate;

(b) adding to the lysate an effective volume of a precipitating solution comprising about 200 mM KCl in about 20 mM Tris-HCl, pH 7.5;

(c) subjecting the mixture to a shearing force capable of shearing the DNA;

(d) forming a SDS-potassium precipitate by cooling the samples to about 4° C. for about 5 min, and collecting the precipitate;

(e) dispersing the precipitate in a solution of about 100 mM KCl and about 20 mM Tris-HCl, at a pH of about 7.5;

(f) heating the dispersed precipitate to about 65° C. for about 10 minutes followed by cooling to about 4° C. for at least about 5 minutes;

(g) washing the precipitate at least once more; and (h) isolating the DNA from the precipitate.

4. BRIEF DESCRIPTION OF THE DRAWINGS

FIG. 1 is a schematic illustration of the principle of the assay of the present invention. The methods of the invention include preparation of K-SDS precipitates of covalently bound DNA-protein complexes, as schematically illustrated, and further detection or quantitation of these complexes using any known method to detect or quantitate DNA.

(FIG. 2B). The background precipitation of fresh samples was 2.5%; following freezing it was reduced to 0.07%.

5. DETAILED DESCRIPTION OF THE INVENTION

The present inventor has developed a new method for detecting DNA-protein crosslinking. This method is capable of detecting DNA-protein complexes induced in animal cells by agents which include, but are not limited to, chromate, formaldehyde, cis- or trans-Pt(II) diammine dichloride (cis-Pt), nickel, alkylating agents, ultraviolet irradiation and gamma radiation, with a level of sensitivity similar to the older alkaline elution method. However, unlike alkaline elution, the method of the present invention does not require time-consuming procedures and specialized equipment. In contrast to known methods, the key advantages of the present method include the capacity to process large numbers of samples and the ability to measure DNA-protein crosslinks without the use of radioactivity. Importantly, the present method is applicable to the measurement of DNA-protein complexes generated in vivo in a living animal.

The present method is an improvement of a K-SDS precipitation assay initially developed by Liu et al., (*J. Biol. Chem.* 258:15365–15370 (1983)) and by Muller and his co-workers (Muller, M. T. *Biochem. Biophys. Res. Commun.* 114:99–106 (1983); Trask, D. K. et al., supra) to detect DNA-topoisomerase complexes.

Improved methods for preparing cellular, nuclear or mitochondrial samples for detection of covalently crosslinked DNA-protein is achieved using a modification of procedures originally developed for quantitating covalent complexes between DNA and the enzymes topoisomerase I and II (Liu et al., supra; Muller, supra). Following treatment of either a sample of cells or an animal with a crosslink-inducing agent, cells are obtained from the culture sample or animal by conventional means.

Any type of cells may be used in accordance with this invention. (See, for example, Sambrook, J. et al., (*MOLECULAR CLONING: A LABORATORY MANUAL*, 2nd Edition, Cold Spring Harbor Press, Cold Spring Harbor, N.Y. (1989); Albers, B. et al., *MOLECULAR BIOLOGY OF THE CELL*, 2nd Ed., Garland Publishing, Inc., New York, N.Y. (1989)). Nonlimiting examples of cells of established cell lines propagated in vitro which may be derived from fibroblasts, lymphoid cells, or tumors include, but are not limited to, CHO, CV-1, NIH-3T3, Vero, HeLa, cells of lymphoid origin, such as myelomas or hybridomas, and their derivatives. Cells freshly harvested from an animal or subjected to short term culture are also useful, for example, leucocytes, lymphocytes and the like.

Following washing, the cells are suspended in a standard buffer, for example, phosphate buffered saline (PBS), preferably at about 4° C. The concentration of cells can be varied according to cell type, cell size, etc., as is well-known to one of ordinary skill in the art. Preferably, cells are lysed at a concentration of about 0.5–1 ×10$^6$ cells per 0.5 ml of lysing solution as described below.

Cells are lysed with a lysing solution containing the detergent sodium dodecyl sulfate (SDS), preferably at a concentration between about 0.5% and about 2.0% (v/v), more preferably at about 2%. Preferably, the SDS solution is buffered in about 20 mM Tris-HCl (pH 7.5) and contains an effective concentration of a proteinase inhibitor, for example, 1 mM PMSF.

Lysed samples may be tested immediately or frozen, for example at −20° C. or −70° C., or lower, for storage.

The freshly lysed samples, or the thawed frozen samples are preferably subjected to vigorous vortexing for a short interval, preferably about 10 seconds, and are warmed for about 10 minutes at a temperature of about 65° C. Thereafter, a solution containing potassium ions, preferably KCl is added. The preferred final concentration of KCl in the preparation of SDS and lysed cells is in the range of about 50 mM to about 100 mM, preferably about 100 mM.

The resulting mixture is then subjected to shearing forces to obtain DNA fragments of uniform length, preferably about 20 kilobases. A preferred method of shearing is by passing the lysate about 5 times through the conical 1 ml tip designed for conventional micropipettes. Other means of similarly shearing DNA are well-known in the art and include passing a cell lysate through a syringe needle. Preferred DNA concentrations for shearing range from about 0.5 to about 30 µg/ml, preferably from about 5 to about 15 µg/ml; concentrations higher than 40 µg/ml should be avoided. Reproducible shearing of DNA is important for optimal sensitivity of the assay.

The potassium ions may be added to the preparation of SDS and lysed cells before the shearing step, as described above, or after the shearing step, as described in FIG. 1. The choice is one of convenience. The SDS-K precipitate is formed by cooling the samples, for example, on ice for about 5 min. The precipitate is then collected using conventional means, such as by centrifugation at 3000 ×g for 5 min. at 4° C. in an Eppendorf microfuge. The pelleted precipitate is then resuspended in an appropriate volume of a buffer solution containing a KCl concentration of about 50 mM to about 100 mM, preferably, about 100 mM. The suspension is performed by pipetting the precipitate several times. To ensure effective washing and shearing of DNA, it is essential to completely disperse the precipitate. The samples may then be heated for about 10 min at about 65° C., chilled on ice and re-centrifuged. This washing step is preferably repeated several times more.

The foregoing describes one embodiment of this invention directed to preparing a sample of tissue, cells, nuclei, or mitochondria for detection or quantitation of DNA-protein complexes contained therein. In another embodiment, the resulting pellet of precipitated material may then be analyzed for its content of protein-linked DNA using any analytical procedure for measuring DNA, for example, by measuring the fluorescence of a fluorescent DNA-binding dye. A preferred dye is Hoechst 33258, due to its high sensitivity.

The amount of DNA-protein crosslinking may be expressed as a DNA-protein crosslinking coefficient (DPC coefficient) calculated as a ratio of % SDS-precipitable DNA in treated cells to % SDS-precipitable DNA in control cells.

It is noteworthy that, unlike the prior art method, the method of the present invention utilizes harsh treatment to dissociate non-covalent DNA-protein binding (e.g., 2% SDS, heat at 65° C.) and involves selective precipitation of stable (covalent) DNA-protein complexes by adding KC1.

Having now generally described the invention, the same will be more readily understood through reference to the following examples which are provided by way of illustration, and are not intended to be limiting of the present invention, unless specified.

6. EXAMPLE: CROSSLINKING OF DNA-PROTEIN IN CULTURED CELLS

6.1. DETECTION OF DNA-PROTEIN CROSSLINKS

DNA-protein crosslinks were detected using a method which represents an improvement of procedures for quantitating covalent complexes between DNA and topoisomerases I and II (Liu et al., supra; Muller, supra). Following treatment with crosslink-inducing agents, cells were scraped with a rubber policeman, washed twice in ice-cold PBS and suspended in ice-cold PBS at a concentration of $1-2 \times 10^7$ cells/ml. Cells (100 μl) were lysed in 1.5 ml Eppendorf tubes in 0.5 ml of a solution of 2% SDS, 1 mM PMSF and 20 mM Tris-HCl (pH 7.5). Lysed samples were frozen at $-20°$ C. or $-70°$ C. Such samples can be stored for at least one month. After thawing, the mixture was vigorously vortexed for 10 sec. and warmed 10 min. at 65° C. Thereafter, 0.5 ml of 200 mM KCl in 20 mM Tris-HCl, pH 7.5, was added, and the mixture was passed through a 1 ml pipet tip 5 times. Reproducible shearing of DNA was important since the uniformity of DNA fragment length influenced the sensitivity of the assay. While the length of the DNA fragments per se is not the key factor, the reproducibility of the shearing step depends on the generation of a similar distribution of DNA fragments in terms of their length.

The SDS-K precipitate was formed by cooling the samples on ice for 5 min. The precipitate was collected by centrifugation at 3000 ×g for 5 min at 4° C. in an Eppendorf microfuge. The pellet was resuspended in 1 ml 100 mM KCl, 20 mM Tris-HCl, pH 7.5, by pipetting 5 times. To ensure effective washing and shearing of DNA, it was essential to completely disperse the precipitate. The samples were heated 10 min at 65° C., chilled on ice and centrifuged 5 min at 3000 ×g. The washing step was repeated twice more.

The resulting pellet was resuspended in 1 ml water and the amount of protein-linked 3H-DNA was determined by placing the samples in 10 ml of the Aquasol and counting radioactivity in a scintillation counter.

Fragments of DNA at the end of the washing and shearing averaged 25 kb in size when obtained from human cells and about 20 kb when obtained from CHO cells. The total amount of $^3$H-DNA was determined as trichloroacetic acid-insoluble material. However, by allowing a longer chase period after [$^3$H]thymidine incorporation, an acid precipitation step was not necessary. A DNA-protein crosslinking coefficient (DPC coefficient) was determined as a ratio of % SDS-precipitable DNA in treated cells to % SDS-precipitable DNA in control cells.

6.2. CELL GROWTH

CHO cells were grown as monolayer cultures in α-minimal essential medium (α-MEM) supplemented with 10% fetal bovine serum, 2 mM L-glutamine and 1% of a standard solution penicillin-streptomycin. Cells were incubated in a humidified atmosphere of 95% air and 5% $CO_2$ at 37° C. Cells were routinely grown to about 60–80% confluence, trypsinized, and replated at a 1:8 dilution. Cells in exponential growth phase were used in all experiments, generally $5-10 \times 10^6$ cells per 150 mm diameter dish. [$^3$H]thymidine was added to the culture in concentrations of 0.5–1.0 mCi/ml to label the DNA. After 24–48 hr, the medium was changed, and 2 hr later the crosslinking agents were added at the indicated concentrations. Cells at a density of about $5-15 \times 10^6$ cells per 150 mm diameter dish were treated with various crosslink inducing agents. The cytotoxic effects of these treatments have been discussed in other publications from the present inventor's laboratory (Miller, C. A. et al., Mol. Carcinogenesis 1:125–133 (1988); Miller, C. A. et al., Mol. Toxicol. 2:11–26 (1989); Miller, C. A. et al., Mutat. Res. 234:97–106 (1990)).

6.3. Cis-Pt Treatment

Figure 2A:
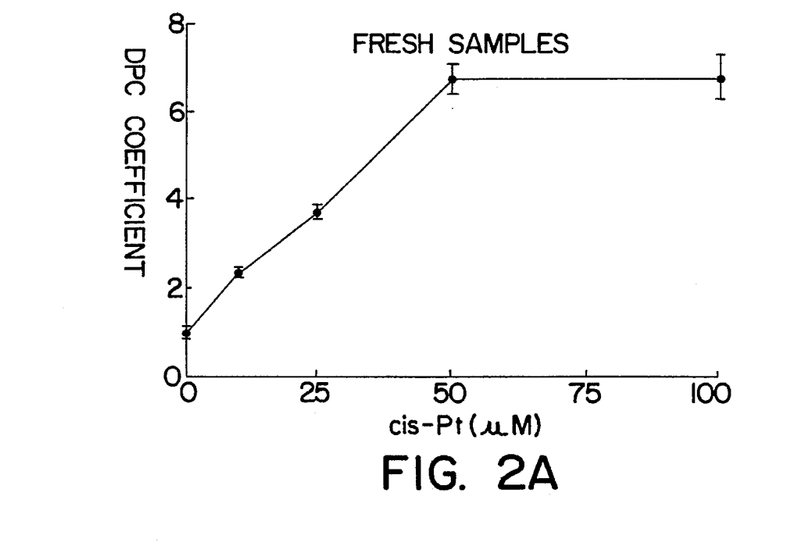
FIGS. 2A and 2B are a set of graphs showing DNA-protein crosslink formation following exposure of CHO cells for 16 hr in complete medium. After scraping and washing, cells were subjected to the K-SDS procedure either immediately (FIG. 2A) or following overnight storage at −70° C.
Figure 2B:
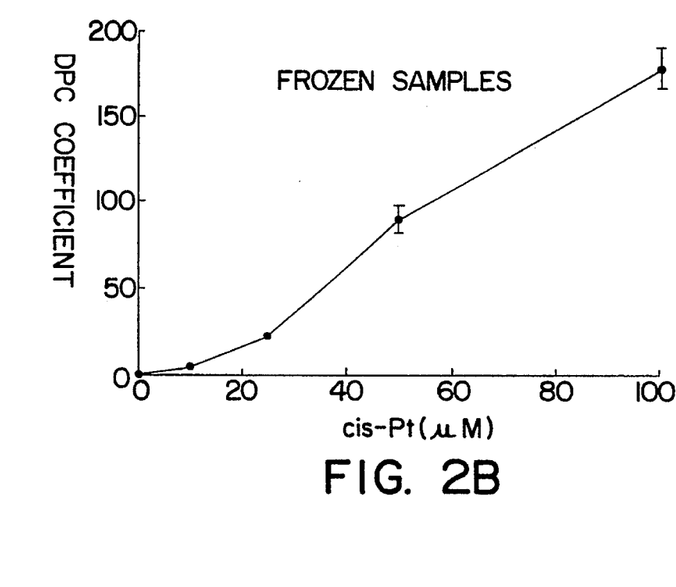

The first series of experiments leading to the present invention were aimed at studying experimental conditions that influenced the efficiency of measurement of crosslinked DNA-protein in cells. To accomplish this, CHO cells were exposed to cis-Pt and tested using different methods for shearing chromosomal DNA (FIGS. 2A and 2B). Significant amounts of DNA-protein crosslinks were induced, in a dose-dependent fashion.

Cells were treated for 16 hr in complete medium. A freeze-thaw procedure (compare FIG. 2A to 2B) was the most effective way to decrease background DNA precipitation. Sonication of samples after storage at $-70°$ C. improved sensitivity of the assay, but shaking the samples using a vortex stirrer was the best approach for disruption of cellular DNA following thawing.

A highly reproducible and sensitive method was found to combine:

a. effective washing procedures (including complete dispersion of SDS-pellet by passing the contents through 1 ml plastic pipet tips (Rainin or Oxford)); and b. vigorous shearing of DNA Use of other brands of 1 ml pipette tips designed for automatic pipettors did not change the results.

The importance of the preparation method is illustrated by comparing the greatest response obtained with cis-platinum with a lesser response (FIG. 2B compared to FIG. 2A).

Frozen samples could be stored at $-20°$ C. or $-70°$ C. without loss of DNA-protein complexes.

Using this assay, a five-fold increase in the amount of crosslinked DNA-protein was obtained following exposure of CHO cells to as low as 10 μM cis-Pt (FIG. 2B). This sensitivity resembled that of alkaline elution (Zwelling, L. A. et al., supra).

6.4. Formaldehyde Treatment

Figure 3:
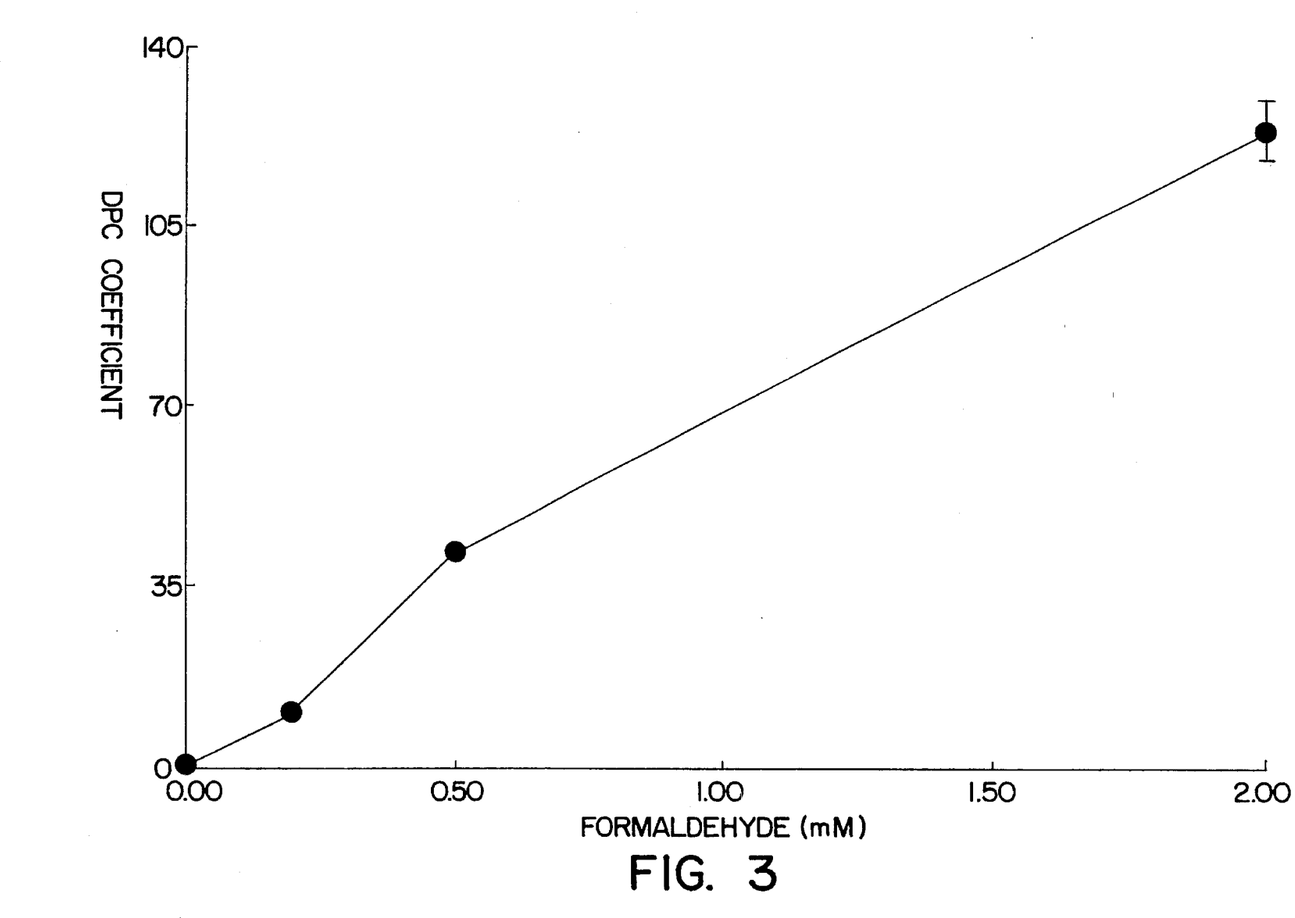
FIG. 3 is a graph showing DNA-protein crosslink formation induced by formaldehyde in CHO cells. Cells were labeled with $^3$H-thymidine for 48 hr, followed by incubation in non-radioactive medium for 2 hr. Cells were treated for 1.5 hr with 0, 0.2, 0.5, or 2 mM formaldehyde in medium without serum, collected by scraping, washed in PBS buffer and subjected to the K-SDS procedure.

Cells were treated for 1.5 hr in serum-free medium. FIG. 3 demonstrates that the assay method of the present invention measured dose-dependent formaldehyde-induced DNA-protein crosslinking. The lowest concentration of formaldehyde tested (0.2 mM) resulted in a ten-fold increase of DNA-protein crosslinks. Formaldehyde has been found to preferentially induce DNA-histone crosslinks (Miller, C. A. et al., 1989, supra). The $K^+$-SDS method was found to be about one order of magnitude more sensitive than a procedure which used antibodies to histone for detecting DNA-protein complexes (Miller, C. A. et al., 1990., supra).

6.5. Chromate Treatment

Cells were treated for 24 hr. in complete medium or for 2 hr. in salt/glucose medium (SGM; 50 mM HEPES, pH 7.2, 100 mM NaCl, 5 mM KCl, 2 mM $CaCl_2$ and 5 mM glucose).

Chromate has been reported to induce DNA-protein crosslinks following treatment of cells in SGM, as well as in complete medium (Sugiyama, M. et al., supra; Chen, Y. et al., supra).

Figure 4A:
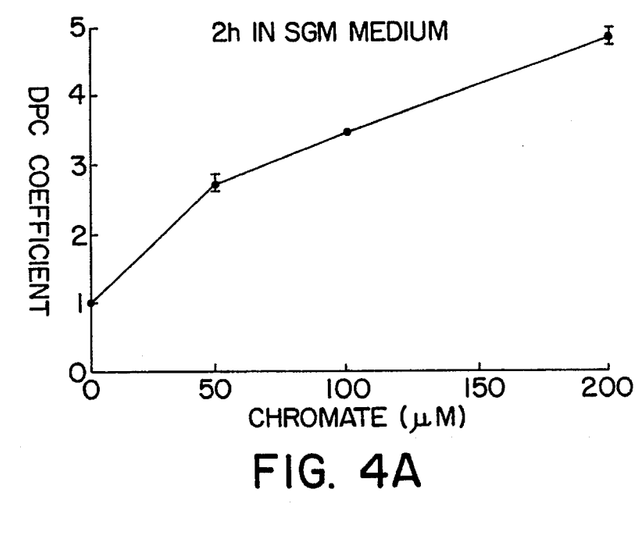
FIGS. 4A and 4B are a set of graphs showing DNA-protein crosslink formation induced by chromate in CHO cells. Cells were radiolabelled with $^3$H-thymidine for 24 hr, followed by incubation in non-radioactive medium for 2 hr. Cells were exposed to potassium chromate (FIG. 4A) in salt/glucose medium for 2 hr or (FIG. 4B) in complete medium for 24 hr.
Figure 4B:
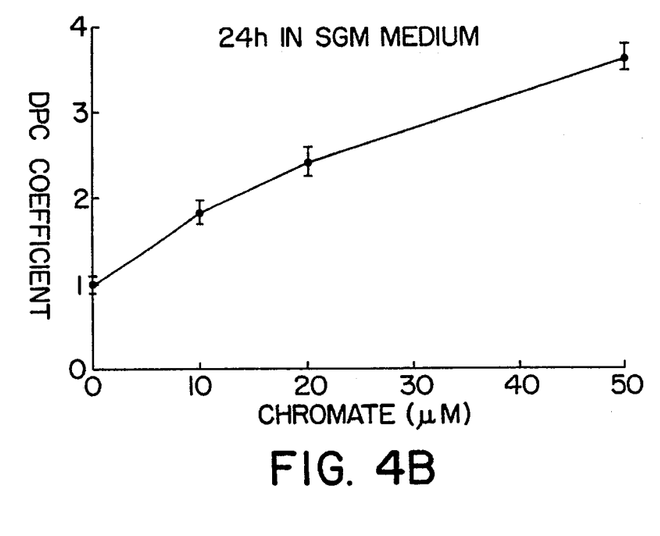

The K-SDS assay of the present invention was used to evaluate chromate-dependent DNA-protein crosslinking in both types of culture media (FIGS. 4A and 4B). Exposure of CHO cells to chromate in complete medium for 24 hr, or exposure in SGM for 2 hr, resulted in the formation of substantial amounts of DNA-protein complexes (FIG. 4). The effect observed was dose-dependent under both experimental conditions, with sensitivity similar to alkaline elution (Chiu, S.-M. et al., *Int. J. Radiat Biol.* 46:681–690 (1984)).

The anionic detergent SDS is known to bind proteins but not DNA. Addition of KCl to SDS solution resulted in the formation of a K-SDS precipitate which was easily recovered by low-speed centrifugation. SDS bound to proteins was crosslinked upon addition of KCl, causing crosslinking of the proteins, Protein-free DNA and protein-bound DNA, therefore, were easily separated since free DNA remained in supernatant while protein-linked DNA was precipitated with the protein-bound SDS when the cation was changed from $Na^+$ to $K^+$. Thus, the amount of DNA in the SDS pellet was a direct measure of crosslinked DNA-protein.

7. EXAMPLE: TREATMENT OF ANIMALS WITH CROSSLINK-INDUCING AGENTS

Since DNA-protein complexes persist once formed, the present inventor postulated that complex formation in WBC as a result of exposure of whole animals to chromate might serve as a useful biological marker of exposure.

Rats and mice were exposed to chromate by intraperitoneal (i.p.) injection (40 mg chromate/kg of body weight) for 3 h, using freshly prepared potassium chromate solutions in physiologic saline. Control animals received equivalent volumes of saline. Animals were sacrificed using pentobarbital, and blood was collected in 15 ml tubes containing 5 mM EDTA as an anticoagulant.

White blood cells (WBC; leucocytes) were isolated using selective lysis of red blood cells by $NH_4Cl$. Blood from 4–5 mice or from two rats was pooled in each tube. The blood was mixed with 0.83% $NH_4Cl$ (pH 7.2) and held at room temperature for 10–15 minutes until lysis of red blood cells was complete. The suspension was centrifuged (10 min, 400 ×g), the pellet was suspended in 10 ml of $NH_4Cl$ solution, and cells again centrifuged for 10 min. This pellet was suspended in 1 ml of lysed solution and the suspension was transferred into 1.5 ml Eppendorf tubes. WBC were pelleted at 1000×g for 3 min at 4° C. The resulting pellet of WBC was resuspended in ice-cold PBS (1–2 ×10$^7$ cells/ml).

The SDS-precipitation assay for crosslinked DNA-protein in WBC was performed as above except that 2–3 blank tubes (cell-free, containing 100 µg BSA) were added to each set of the samples. The final SDS-K precipitate was resuspended in 1 ml 100 mM KCl, 10 mM EDTA, 20mM Tris-HCl, pH 7.5. Proteinase K was added to a final concentration 0.2 mg/ml and the suspension was incubated for 3 hr at 50° C. SDS was precipitated by chilling samples on ice. 100 µg BSA was added to each sample to facilitate precipitation of SDS. The SDS precipitate was collected by centrifugation for 10 min at 10,000 ×g at 4° C. The supernatant was used to determine the amount of DNA, using the fluorescent dye Hoechst 33258 (Labarca, C. et al., *Anal. Biochem.* 102:344–352 (1980); Cesarone, C. F. et al., *Anal. Biochem.* 100:188–197 (1979)).

The supernatant (~1 ml) containing DNA was transferred to the 12 ×75 mm borosilicate disposable culture tubes (Fisher Scientific, PA) and mixed with 1 ml of freshly prepared Hoechst dye reagent (200 ng/ml), in 20 mM Tris-HCl, pH 7.5. The tubes were briefly vortexed and allowed to stand for 30 min in the dark. To determine the total amount of DNA in the samples, the cells were lysed in 1 ml of 2M NaCl, 20 mM Tris-HCl, pH 7.5, vortexed and then mixed with the fluorescent reagent. A stock Hoechst solution (1 mg/ml in $H_2O$ or in 20 mM Tris-HCl buffer, pH 7.5) could be stored in the dark at 4° C. as previously reported (Cesarone et al., supra), but the absolute value of fluorescence decreased during storage time. Thus, concurrent determination of the fluorescence of the samples and standard DNA probes was carried out. For maximal sensitivity, a freshly prepared stock of Hoechst solution was used. Fluorescent measurements were made using a Model 450 digital fluorometer (Sequoia-Turner Corporation, CA) with NB 360 excitation and SC450 emission filters.

Figure 5:
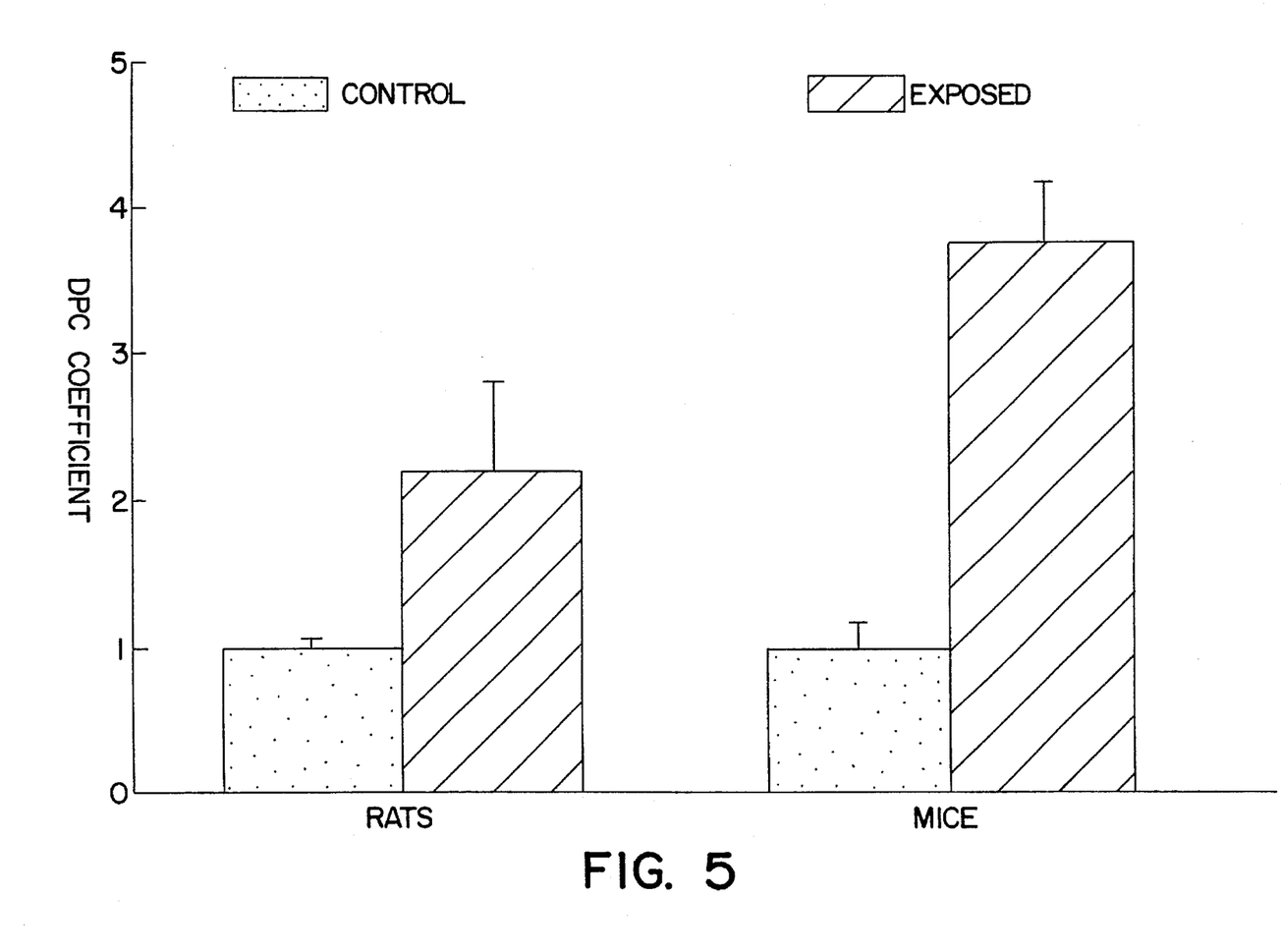
FIG. 5 is a graph showing DNA-protein crosslinks in white blood cells (WBC) following in vivo exposure of animals to potassium chromate. WBC were isolated from rats or mice 3 hours after intraperitoneal (i.p.) exposure to potassium chromate at 40 mg/kg. Crosslinked DNA-protein were determined using the K-SDS assay.

FIG. 5 presents the results of measurement of crosslinked DNA-protein from WBC obtained from rats or mice exposed for 3 hr to 40 mg/kg of potassium chromate. This dose induced significant amounts of crosslinked DNA-protein in both rat and mouse WBC with mice showing higher levels. This result corresponds to the higher content of chromate found in mouse WBC compared to rat WBC after i.p. administration of chromate (Kargacin, B. et al., *Abstr. Fourth Ann. Meeting Soc. Toxicol.* 12:310, abstr. #1200 (1992)).

The exposure conditions were similar to those previously tested in the present inventor's laboratory for detection of crosslinked DNA-protein using the alkaline elution assay or antibodies to p97 protein crosslinked with DNA (Coogan, T. P. et al., *Toxicol. Appl. Pharmacol.* 109:60–72 (1991)). However, these other methods failed to detect DNA-protein complexes in rat WBC from animals exposed to chromate in vivo, illustrating that the method of the present invention is more sensitive than others (Kohn, K. W. et al., 1981, supra) and can be utilized to detect formation of DNA-protein complexes in vivo.

In summary, an efficient method for measuring crosslinked DNA-protein was successfully applied to assessing the crosslinking activity of agents that differ in both their mechanism of action and in the profile of proteins crosslinked (Miller, C. A. et al., 1989, supra). The presence of crosslinked DNA-DNA and DNA strand breaks did not influence measurements using the present assay since the method did not involve unwinding of DNA strands. Thus, endogenous levels of double strand breaks contributed negligibly, if at all, because of the vigorous shearing of DNA that was part of the present procedure.

The assay disclosed herein offers advantages in being inexpensive, simple to perform, and sensitive for determining DNA-protein crosslinks in cells. In other applications, this procedure may be used to recover the components involved in DNA-protein complex formation.

8. EXAMPLE: DETECTION OF DNA-PROTEIN CROSSLINKS IN METAL WELDERS

Welders are exposed to fumes containing various metal oxides and salts (IARC Monograph on the *Evaluation of Carcinogenic Risk to Humans. Chromium, Nickel and Welding,* Vol. 48, pp. 49–508, 1990, Lyon, France). Fumes from stainless steel and other alloys contain Cr and Ni compounds in high concentrations as compared to mild steel. Welding fumes are retained by the lungs and are released slowly, thereby contributing to elevated Cr and Ni concentrations observed in blood and urine of stainless steel welders (IARC Monograph, supra; Bonde, J. P. et al., *Arch. Environ. Health* 46:225–229 (1991); Sjogren, B. et al., *Int. Arch. Occup. Environ. Health* 51:347–354 (1983). There is ample evidence that inhaled Cr and Ni are human carcinogens. The present study was thus directed to the use of the assays described above for detecting DNA-protein crosslinks in peripheral white blood cells of railroad welders, a population occupationally exposed to small amounts of Cr and Ni through inhalation of welding fumes.

8.1. Methods

The sample tested consisted of 21 railroad arc welders and 26 unexposed controls of similar age and smoking habits. Two welders and five controls were Afro-Americans; all others were Caucasians.

Venous blood was drawn into heparinized Vacutainer tubes and the white blood cells immediately isolated by selectively lysing the erythrocytes with ammonium chloride. The resulting cell pellets were resuspended in storage medium (70% Minimal Essential Medium supplemented with 20% fetal bovine serum and 10% dimethyl sulfoxide, and placed at $-70°$ C. Frozen cells were transported to the laboratory on dry ice. After thawing, cells were washed twice in ice-cold PBS and resuspended in PBS at $10–20 \times 10^6$ cells/ml.

DNA-protein crosslinks were detected using the method described above. FIG. 1 summarizes the principle of the assay. DNA was sheared by a series of pipetting steps as described above which yielded fragments of about 25 kb of human DNA. The final SDS-potassium precipitate was resuspended in 1 ml of 100 mM KCl, 10 mM Tris-HCl (pH 7.5) followed by addition of proteinase K to a concentration of 0.2 mg/ml. The suspension was placed for 3 hr at 50° C. with occasional shaking. SDS was precipitated by chilling the samples on ice and 100 μg BSA was added to each sample to facilitate precipitation. The SDS precipitate was collected by centrifugation at 10,000 ×g for 10 min at 4° C.

The supernatant containing DNA was transferred to 12×75 borosilicate tubes and mixed with 1 ml of freshly prepared Hoechst fluorescent dye reagent (200 ng/ml)(Sigma Chemical Company, St. Louis, Mo.) in 20 mM Tris-HCl (pH 7.5). The tubes were vortexed and incubated in the dark for 20–30 min. To determine the total amount of DNA in the samples, the cells were lysed in 1 ml 2M NaCl, 20 mM Tris-HCl (pH 7.5), vortexed and mixed with the fluorescent reagent. The fluorescence of the samples was monitored standard DNA probes. Fluorescence was measured using a Model 450 digital fluorometer ((Sequiola-Turner Corporation, California) with NB360 excitation and SC450 emission filters.

8.2. Results and Discussion

Figure 6:
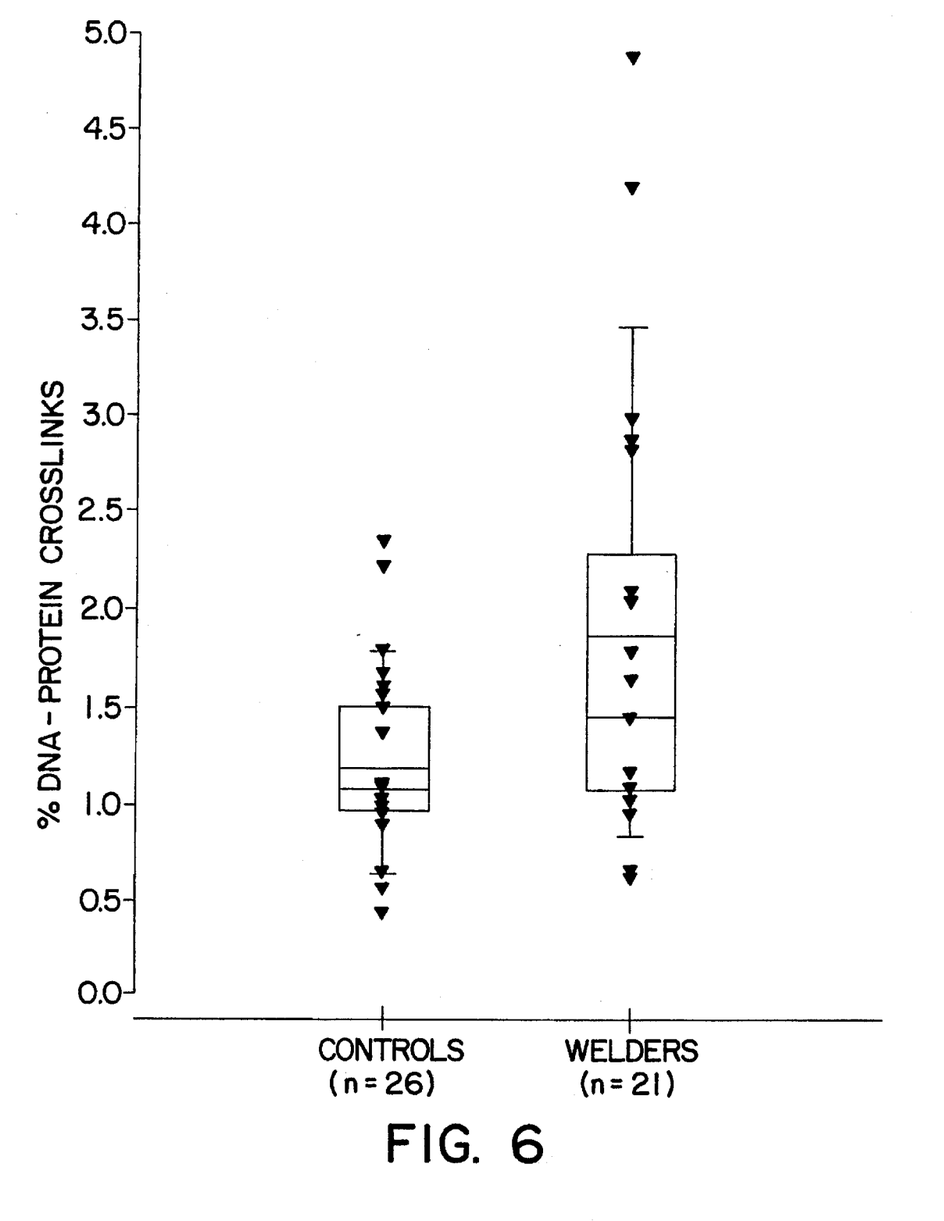
FIG. 6 shows individual DNA-protein cross link (DPC) values among 21 railroad welders and 26 controls. The box plots display the 10th, 25th, 50th, 75th and 90th percentiles as error bars; the dotted bar displays the mean.

The welders tested had been exposed full time to welding fumes from mild steel welding on railroad tracks or in railroad shops for 6 or more months. None reported exposure to stainless steel welding in recent time. Controls were office workers, supervisory field railroad workers, union representatives, janitors and laboratory technicians. The characteristics of the subjects and the results are presented in Table I. Despite some overlap (FIG. 6), levels of DNA-protein crosslinks were more elevated among welders (Mean=1.85%; SD=1.14) than unexposed controls (Mean 1.17%; SD=0.46) and were statistically significant (p=0.01). Of the 21 welders, 5 (24%) showed crosslink values above the upper range of the entire control distribution. Crosslink values did not appear to vary with age, smoking status, body weight or race.

TABLE I

SELECTED CHARACTERISTICS OF STUDY SUBJECTS AND INDIVIDUAL DNA-PROTEIN CROSSLINK LEVELS IN WHITE BLOOD CELLS

| # | Age | Race | Current Smoker | % DPC Mean* | S.D.** |
|---|---|---|---|---|---|
| (a) Controls | | | | | |
| 1 | 48 | AA | N | 1.08 | 0.18 |
| 2 | 63 | C | N | 1.09 | 0.25 |
| 3 | 44 | C | Y | 1.10 | 0.06 |
| 4 | 40 | C | N | 1.10 | 0.21 |
| 5 | 50 | C | N | .93 | 0.24 |
| 6 | 52 | C | N | 1.11 | 0.25 |
| 7 | 56 | C | N | .98 | 0.10 |
| 8 | 47 | C | N | 2.20 | 0.77 |
| 9 | 38 | C | N | .88 | 0.14 |
| 10 | 34 | C | N | 1.55 | 0.13 |
| 11 | 42 | C | N | .55 | 0.06 |
| 12 | 36 | C | Y | 1.04 | 0.39 |
| 13 | 41 | C | N | 1.66 | 0.22 |
| 14 | 41 | AA | Y | 1.49 | 0.59 |
| 15 | 31 | AA | Y | 1.36 | 0.36 |
| 16 | 56 | AA | Y | 1.02 | 0.24 |
| 17 | 51 | AA | N | .99 | 0.15 |
| 18 | 36 | C | Y | .65 | — |
| 19 | 44 | C | N | .42 | 0.14 |
| 20 | 35 | C | N | 2.33 | 0.63 |
| 21 | 34 | C | Y | .97 | 0.19 |
| 22 | 39 | C | Y | .62 | 0.03 |
| 23 | 45 | C | N | 1.02 | 0.12 |
| 24 | 42 | C | N | 1.78 | 0.33 |
| 25 | 30 | C | N | .95 | 0.08 |
| 26 | 35 | C | Y | 1.59 | 0.47 |
| (b) Welders | | | | | |
| 1 | 38 | C | N | 1.77 | 0.25 |
| 2 | 44 | C | N | 1.02 | 0.09 |
| 3 | 39 | C | Y | 1.44 | 0.53 |
| 4 | 33 | AA | Y | .65 | 0.17 |
| 5 | 35 | C | Y | 2.08 | 0.31 |
| 6 | 39 | C | Y | .61 | 0.13 |
| 7 | 27 | C | N | 2.86 | 0.26 |
| 8 | 43 | C | Y | 4.19 | 2.46 |
| 9 | 39 | C | Y | 4.88 | 0.16 |
| 10 | 43 | AA | N | 1.08 | 0.30 |
| 11 | 41 | C | Y | 2.03 | 0.40 |
| 12 | 36 | C | N | 2.81 | — |
| 13 | 35 | C | N | .94 | 0.12 |
| 14 | 37 | C | N | 1.43 | 0.25 |
| 15 | 39 | C | Y | 1.25 | 0.29 |
| 16 | 34 | C | N | 2.97 | 0.21 |
| 17 | 35 | C | Y | 1.01 | 0.11 |
| 18 | 53 | C | N | 2.07 | 0.37 |
| 19 | 38 | C | Y | 1.15 | 0.25 |
| 20 | 37 | C | N | 1.07 | 0.60 |
| 21 | 38 | C | Y | 1.63 | 0.39 |

*Average of 2–4 assays in the same individual; for subjects #18 and #38, only one assay was available
**The coefficient of variation (the within-subject S.D. divided by the mean) was 33%.

Cr and Ni levels were measured by atomic absorption spectroscopy in the blood of all controls and welders. Ni levels were not elevated whereas Cr levels were slightly, though not statistically significantly, elevated. In general, Ni and Cr levels were at levels which were barely detectable. Thus, the observed increase in crosslinking cannot definitively be related to Ni or Cr levels. A previous study showed some elevation of DNA-protein crosslinks in lymphocytes of welders using alkaline elution (Popp et al., 1991, supra).

The presence of a protein covalently bound to DNA is expected to act as an impediment to replication of DNA, leading to deletions of transient genetic lesions which are not repaired. This has been observed in studies of Chinese hamster X chromosomes, where Ni compounds resulted in deletion of the long q arm of the X chromosome (Conway, K. et al., *Cancer Res.* 49:6032–6038 (1990); Sen, P. et al., *Cancer Res.* 45:2320–2325 (1985)). Trivalent Cr crosslinks certain amino acid residues to DNA, including tyrosine, histidine, threonine and methionine (Lin, X. et al., *Carcinogenesis,* 1992; Salnikow, K. et al., *Carcinogenesis,* 1992)); glutathione was also crosslinked to DNA via its cysteine portion. The structure of the Ni-induced crosslinks are likely to resemble those known to occur following radiation or exposure to other oxygen radicals (Simic, M. et al., *Biochemistry* 24:233–236 (1985)).

Thus, the present study demonstrates that welders have an elevation in a biomarker related to Ni and Cr exposure in their leukocytes. This lesion is also very likely to be present in other tissues, such as the lungs, which are subjected to even greater exposure. This higher burden of DNA-protein crosslinks in welders serves not only as a biomarker of exposure to a crosslinking agent (e.g., Ni or Cr) but also may serve as an early indicator of other potential genotoxic consequences such as cancer.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for preparing a sample of cells, nuclei or mitochondria for the detection or quantitation of covalently bound DNA-protein complexes contained therein, comprising:

(a) preparing a lysate of the cells, nuclei or mitochondria of said sample in a lysing solution containing at least about 0.5% (v/v) sodium dodecyl sulfate such that said lysate contains DNA at a concentration between about 0.5 µg/ml and 40 µg/ml;

(b) adding to said lysate, before or after step (c), below, an effective volume of a precipitating solution comprising about 200 mM KCl in about 20 mM Tris-HCl, pH 7.5;

(c) subjecting the mixture to a shearing force which shears said DNA to fragments of homogeneous size;

(d) forming a sodium dodecyl sulfate-potassium precipitate by cooling the samples to about 4° C. for about 5 minutes, and collecting the precipitate;

(e) dispersing said precipitate in a solution of about 100 mM KCl and about 20 mM Tris-HCl, at a pH of about 7.5;

(f) heating said dispersed precipitate to about 65° C. for about 10 minutes followed by cooling to about 4° C. for at least about 5 minutes;

(g) washing said precipitate at least once more in the solution of step (e); and (h) resuspending said precipitate in a solution for detecting or quantitating DNA, thereby preparing said sample.

2. A method of claim 1 wherein, after step (a), said treated sample or said lysate is frozen of about −20° C. or less and stored frozen prior to performing the remaining steps.

3. A method of claim 1 wherein the lysing solution of step (a) is a buffer at a pH of about 7.5 containing about 2% (v/v) sodium dodecyl sulfate.

4. A method according to claim 1 wherein said shearing of step (c) is performed under conditions which yield fragments of DNA having an average length of about 20 kilobases.

5. A method for detecting or quantitating covalently bound DNA-protein complexes in a sample of cells, nuclei or mitochondria, comprising (a) preparing said sample according to claim 2; and (b) detecting or quantitating the DNA in the solution of step (h).

6. A method for detecting the ability of an agent to induce the formation of covalently bound DNA-protein complexes of cells, comprising:

(a) treating said cells with said agent;

(b) detecting or quantitating said complexes in said treated cells using a method according to claim 5, (c) detecting or quantitating said complexes in a control sample of cells not treated with said agent using a method according to claim 5, and (d) comparing the results of step (b) and step (c), wherein an increase in said complexes in said treated cells compared to said control cells is a measure of the ability of said agent to induce the formation of said DNA-protein complexes.

7. A method for detecting or quantitating covalently bound DNA-protein complexes in an animal, comprising:

(a) obtaining from an animal suspected of having said DNA-protein complexes a sample of cells; and (b) detecting or quantitating said complexes in said cells by a method according to claim 5.

8. A method according to claim 7 wherein said cells are white blood cells.

9. A method according to claim 7 wherein said animal is a human.

10. A method according to claim 7, wherein said lysing solution is a buffer at a pH of about 7.5 containing about 2% (v/v) sodium dodecyl sulfate.

11. A method for determining the ability of an agent to induce the formation of covalently bound DNA-protein complexes in a non-human animal, comprising:

(a) treating said animal with said agent;

(b) detecting or quantitating said complexes in said treated animal using a method according to claim 7;

(c) detecting or quantitating DNA-protein complexes in a control animal not treated with said agent using a method according to claim 7; and (d) comparing the results of step (b) and step (c), wherein an increase in said complexes in said treated animal is a measure of the ability of said agent to induce the formation of said DNA-protein complexes.

12. A method for determining whether an animal has been exposed to an agent capable of including DNA-protein crosslinking, comprising detecting in said animal the presence of, or measuring the quantity of, covalently bound DNA-protein complexes by a method according to claim 7.

13. A method according to claim 12 wherein said agent is selected from the group consisting of ultraviolet irradiation, gamma radiation, an alkylating agent, formaldehyde, nickel, chromate, and cis- or trans-Pt(II) diammine dichloride.

14. A method according to claim 12 wherein said animal is a human.

15. A method of isolating from a sample of cells, nuclei or mitochondria, DNA having covalently bound thereto a protein, comprising:

(a) preparing a lysate of the cells, nuclei or mitochondria of said sample in a lysing solution containing at least about 0.5% (v/v) sodium dodecyl sulfate such that said lysate contains DNA at a concentration between about 0.5 µg/ml and 40 µg/ml;

(b) adding to said lysate, before or after step (c), below, an effective volume of a precipitating solution comprising about 200 mM KCl in about 20 mM Tris-HCl, pH 7.5;

(c) subjecting the mixture to a shearing force which shears said DNA to fragments of homogeneous size;

(d) forming a sodium dodecyl sulfate-potassium precipitate by cooling the samples to about 4° C. for about 5 minutes, and collecting the precipitate;

(e) dispersing said precipitate in a solution of about 100 mM KCl and about 20 mM Tris-HCl, at a pH of about 7.5;

(f) heating said dispersed precipitate to about 65° C. for about 10 minutes followed by cooling to about 4° C. for at least about 5 minutes;

(g) washing said precipitate at least once more in the solution of step (e); and (h) isolating the DNA from said precipitate.

16. A method for preparing a sample of cells, nuclei or mitochondria for the detection or quantitation of covalently bound DNA-protein complexes contained therein, comprising:

(a) preparing a lysate of the cells, nuclei or mitochondria of said sample in a lysing solution containing at least about 0.5% (v/v) sodium dodecyl sulfate such that said lysate contains DNA at a concentration between about 0.5 µg/ml and 40 µg/ml;

(b) subjecting the lysate to a shearing force which shears said DNA to fragments of homogeneous size and, before or after said shearing, adding potassium ions to a final concentration at least equimolar to the concentration of sodium dodecyl sulfate to form a sodium dodecyl sulfate-potassium precipitate;

(c) heating, cooling and washing said precipitate in the presence of a concentration of potassium ions sufficient to maintain said precipitate insoluble thereby preparing said sample for detecting or quantitating said complexes.

17. A method for detecting or quantitating covalently bound DNA-protein complexes in a sample of cells, nuclei or mitochondria, comprising:

(a) preparing said sample according to claim 16, and (b) detecting or quantitating the DNA in said precipitate.

18. A method for determining the ability of an agent to induce the formation of covalently bound DNA-protein complexes in a sample of cells, comprising:

(a) treating said cells with said agent;

(b) detecting or quantitating said complexes in said treated cells using a method according to claim 17;

(c) detecting or quantitating said complexes in a control sample of cells not treated with said agent using a method according to claim 17; and (d) comparing the results of step (b) and step (c), wherein an increase in said complexes in said treated cells is a measure of the ability of said agent to induce the formation of said DNA-protein complexes.

19. A method for detecting or quantitating covalently bound DNA-protein complexes in an animal, comprising:

(a) obtaining from an animal suspected of having said DNA-protein complexes a sample of cells; and (b) detecting or quantitating said complexes in said cells by a method according to claim 17.

20. A method according to claim 19 wherein said animal is human.

21. A method for determining the ability of an agent to induce the formation of covalently bound DNA-protein complexes in a non-human animal, comprising:

(a) treating said animal with said agent;

(b) detecting or quantitating said complexes in said treated animal of step (a) using a method according to claim 19;

(c) detecting or quantitating DNA-protein complexes in a control animal not treated with said agent using a method according to claim 19; and (d) comparing the results of step (b) and step (c), wherein an increase in said complexes in said treated animal is a measure of the ability of said agent to induce the formation of said DNA protein complexes.

22. A method for preparing a sample of cells, nuclei or mitochondria for the detection or quantitation of covalently bound DNA-protein complexes contained therein, comprising:

(a) preparing a lysate of the cells, nuclei or mitochondria of said sample in a lysing solution containing at least about 0.5% (v/v) sodium dodecyl sulfate such that said lysate contains DNA at a concentration between about 0.5 µg/ml and 40 µg/ml;

(b) adding to said lysate, before or after step (c) below, an effective volume of a precipitating solution comprising about 200 mM KCl in about 20 mM Tris-HCl, pH 7.5;

(c) subjecting the mixture to a shearing force which shears said DNA to fragments of homogeneous size;

(d) forming a sodium dodecyl sulfate-potassium precipitate by cooling the samples to about 4° C. for about 5 minutes, and collecting the precipitate;

(e) dispersing said precipitate in a solution of about 100 mM KCl and about 20 mM Tris-HCl, at a pH of about 7.5;

(f) heating said dispersed precipitate to about 65° C. for about 10 minutes followed by cooling to about 4° C. for at least about 5 minutes;

(g) washing and resuspending said precipitate at least once more in the solution of step (e);

(h) adding to said resuspended precipitate a protease enzyme at a concentration and for a time sufficient to digest DNA cross-linked protein;

(i) precipitating the sodium dodecyl sulfate by cooling the suspension and adding protein at a concentration effective to facilitate said precipitation; and (j) obtaining the supernatant from step (i) for detecting or quantitating DNA, thereby preparing said sample.

23. A method according to claim 22, wherein said protease of step (h) is proteinase K at a final concentration of about 0.2 mg/ml.

24. A method according to claim 22, wherein said protein of step (i) is bovine serum albumin at a final concentration of at least about 100 μg/ml.

25. A method according to claim 22, wherein said protease of step (h) is proteinase K at a final concentration of about 0.2 mg/ml and said protein of step (i) is bovine serum albumin at a final concentration of about 100 μg/ml.

26. A method for detecting or quantitating covalently bound DNA-protein complexes in a sample of cells, nuclei or mitochondria, comprising:

(a) preparing said sample according to claim 22; and (b) detecting or quantitating the DNA in the supernatant of step (j).

* * * * *